US010105360B2

(12) United States Patent
Rey et al.

(10) Patent No.: US 10,105,360 B2
(45) Date of Patent: *Oct. 23, 2018

(54) METHOD AND COMPOSITION FOR THE TREATMENT OF OPIOID INDUCED CONSTIPATION

(71) Applicant: Develco Pharma Schweiz AG, Pratteln (CH)

(72) Inventors: Hélène Rey, Kembs (FR); Olaf Mundszinger, Efringen-Kirchen (DE); Isabelle Golfier, Bantzenheim (FR); Silvia Jakob, Bernau (DE); Oliver Rusch, Basel (CH)

(73) Assignee: DEVELCO PHARMA SCHWEIZ AG, Pratteln (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/255,868

(22) Filed: Sep. 2, 2016

(65) Prior Publication Data
US 2017/0087150 A1 Mar. 30, 2017

Related U.S. Application Data

(63) Continuation-in-part of application No. 14/563,555, filed on Dec. 8, 2014, now Pat. No. 9,456,986.

(30) Foreign Application Priority Data

Dec. 11, 2013 (EP) .................... 13005759
Dec. 11, 2013 (EP) .................... 13005760
Dec. 11, 2013 (EP) .................... 13005761

(51) Int. Cl.
*A61K 9/20* (2006.01)
*A61K 31/485* (2006.01)
*A61K 9/00* (2006.01)
*A61K 45/06* (2006.01)
*A61K 9/28* (2006.01)
*A61K 9/24* (2006.01)

(52) U.S. Cl.
CPC .......... *A61K 31/485* (2013.01); *A61K 9/0053* (2013.01); *A61K 9/0056* (2013.01); *A61K 9/209* (2013.01); *A61K 9/2013* (2013.01); *A61K 9/2027* (2013.01); *A61K 9/2086* (2013.01); *A61K 9/28* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 8,846,090 B2 * | 9/2014 | Brogmann | A61K 9/1617 424/464 |
| 9,456,986 B2 | 10/2016 | Rey et al. | |
| 2013/0090349 A1 | 4/2013 | Geissler et al. | |
| 2015/0108033 A1 * | 4/2015 | Vamvakas | A61K 9/4866 206/531 |
| 2015/0216806 A1 * | 8/2015 | Borody | A61K 35/741 424/456 |
| 2015/0238420 A1 | 8/2015 | Rey et al. | |

FOREIGN PATENT DOCUMENTS

| | | |
|---|---|---|
| DE | 4325465 A1 | 2/1995 |
| EP | 2425825 A1 | 3/2012 |
| WO | WO-95/20947 A1 | 8/1995 |
| WO | WO-98/25613 A2 | 6/1998 |
| WO | WO-03/007802 A2 | 1/2003 |
| WO | WO-2009/085778 A1 | 7/2009 |
| WO | WO-2011/117306 A1 | 9/2011 |
| WO | WO-2012/052169 A2 | 4/2012 |

OTHER PUBLICATIONS

Hermanns K. et al.: "Prolonged-release oxycodone/naloxone in the treatment of neuropathic pain: results from a large observational study" Expert Opinion on Pharmacotherapy, vol. 13, No. 3,(2012), pp. 299-311.

Meissner W. et al.: "A randomised controlled trial with prolonged-release oral oxycodone and naloxone to prevent and reverse opioid-induced constipation", European Journal of Pain, vol. 13, No. 1, (2009), pp. 56-64.

European Search Report dated Oct. 26, 2016 by the European Patent Office for EP Application No. 16186993.8, (Applicant-Develco Pharma Schweiz) (9 pages).

European Pharmacopoeia 7.3, 2.9.3 "Dissolution Test for Solid Dosage Forms" (2012) (7 pages).

(Continued)

*Primary Examiner* — Susan T Tran

(74) *Attorney, Agent, or Firm* — Ballard Spahr LLP

(57) ABSTRACT

The invention relates to a method of treatment using a solid oral pharmaceutical dosage form comprising an opioid receptor antagonist for use in the treatment of opioid induced constipation comprising the opioid antagonist equivalent to 24 mg of naloxone hydrochloride as twice daily formulation or equivalent to 48 mg of naloxone hydrochloride as once daily formulation, characterized in that the opioid antagonist has a rapid first pass metabolism with a plasma half-life of 2 hours or less in humans within the first 3 hours of oral administration of a solution, wherein the steady state pharmacokinetics result in a constant level of naloxone in the bloodstream, wherein the pharmacokinetics are independent of whether the dosage is administered once or twice daily, wherein the oral dosage form releases the opioid antagonist in a prolonged manner, wherein the in vitro release rate of the opioid antagonist measured using the paddle stirrer method according to Ph. Eur. at 75 rpm in 1000 ml 0.1 N hydrochloric acid at 37° C., is 15%±5% in 1 h, is 26%±5% in 3 h, is 40%±5% in 6 h, is 55%±7% in 10 h, is 67%±8% in 15 h, and is 78%±10% in 20 h.

20 Claims, 5 Drawing Sheets

(56) References Cited

OTHER PUBLICATIONS

Figure 1:
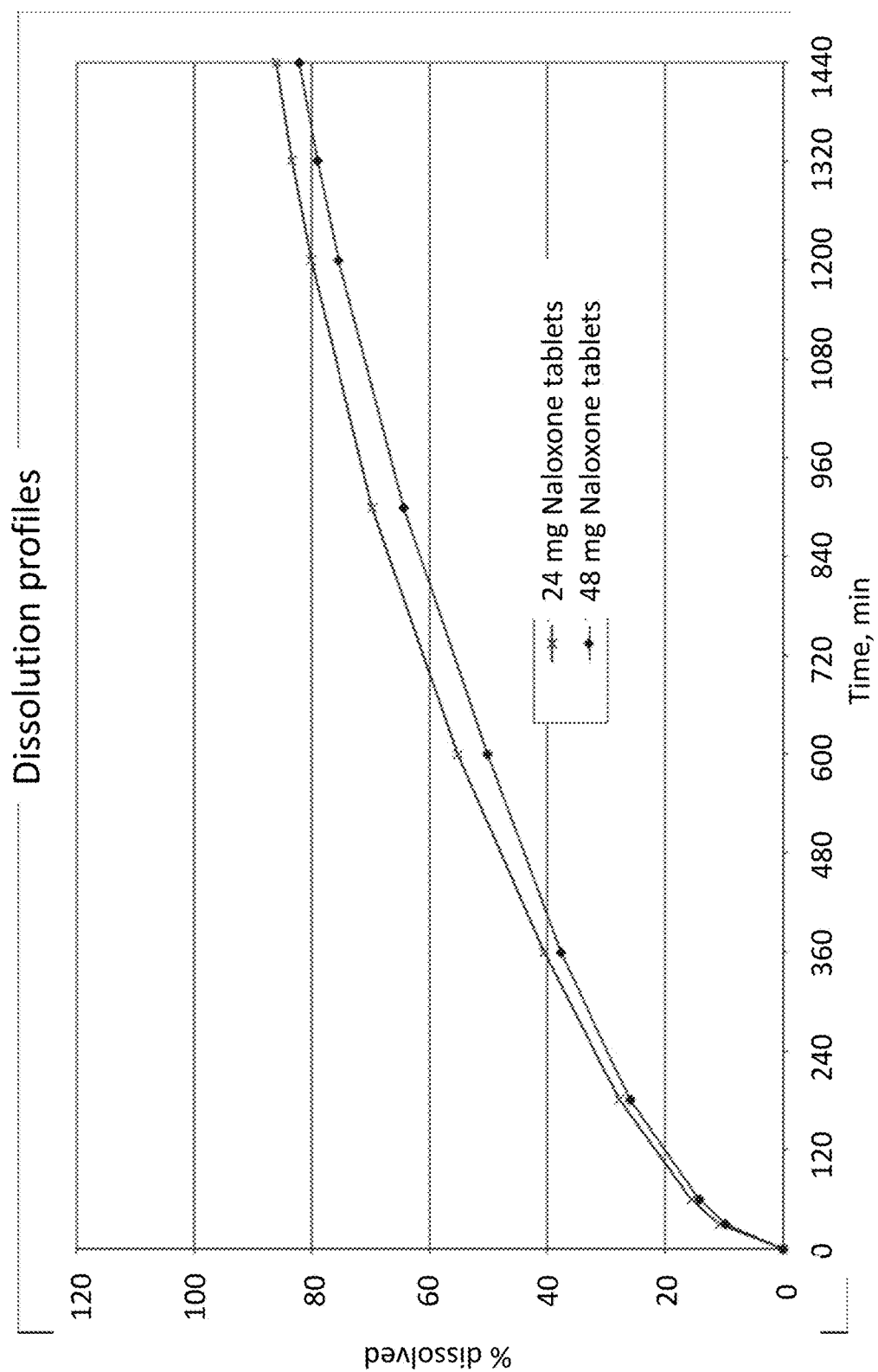

European Pharmacopoeia 7.7, 4.1.3 "Buffer Solutions" (2013) (6 pages).
Shah V. et al "In Vitro Dissolution Profile Comparison—Statistics and Analysis of the Similarity Factor f2", Pharm Res. (1998) 15(6):889-96.
Preliminary Amendment dated Mar. 23, 2015 to the U.S. Patent and Trademark Office for U.S. Appl. No. 14/563,555, which was filed Dec. 8, 2014 and granted as 9,456,986 on Oct. 4, 2016 (Applicant—Develco Pharma Schweiz AG; Inventor—Helene Rey et al) (7 pages).
Non Final Rejection dated Nov. 19, 2015 by the U.S. Patent and Trademark Office for U.S. Appl. No. 14/563,555, which was filed Dec. 8, 2014 and granted as 9,456,986 on Oct. 4, 2016 (Applicant—Develco Pharma Schweiz AG; Inventor—Helene Rey et al) (4 pages).
Response to Non Final Rejection dated Feb. 16, 2016 to the U.S. Patent and Trademark Office for U.S. Appl. No. 14/563,555, which was filed Dec. 8, 2014 and granted as 9,456,986 on Oct. 4, 2016 (Applicant—Develco Pharma Schweiz AG; Inventor—Helene Rey et al) (8 pages).
Notice of Allowance dated Jun. 2, 2016 by the U.S. Patent and Trademark Office for U.S. Appl. No. 14/563,555, which was filed Dec. 8, 2014 and granted as 9,456,986 on Oct. 4, 2016 (Applicant—Develco Pharma Schweiz AG; Inventor—Helene Rey et al) (9 pages).
Issue Notification dated Sep. 14, 2016 by the U.S. Patent and Trademark Office for U.S. Appl. No. 14/563,555, which was filed Dec. 8, 2014 and granted as 9,456,986 on Oct. 4, 2016 (Applicant—Develco Pharma Schweiz AG; Inventor—Helene Rey et al) (1 page).

\* cited by examiner

METHOD AND COMPOSITION FOR THE TREATMENT OF OPIOID INDUCED CONSTIPATION

FIELD OF THE INVENTION

The present invention is in the field of medicine. In particular in the field of opioid therapy and the prevention or alleviation of side effects. More in particular the invention is in the field of treatment of opioid induced constipation and constipation in general.

BACKGROUND

Opioids provide analgesia trough binding to μ-opioid receptors in the central nervous system (CNS). In addition to acting centrally, opioid agonists also act peripherally, e.g. in the GI-tract through binding to opioid receptors in the enteric nervous system (ENS) leading to disruption of bowel motility and causing a variety of deleterious effects including delayed intestinal transit time, decreased peristalsis, increased water reabsorption, and decreased gastrointestinal secretions.

Peripheral opioid-mediated GI side effects occur frequently and can limit the utility of opioids. The peripheral deleterious effects of opioids give rise to a variety of GI symptoms often referred to as opioid-induced bowel dysfunction (OBD). The most frequent and often most bothersome symptom is opioid-induced constipation (OIC), which occurs in a substantial proportion of patients with incidences ranging from 15-90%. In addition to OIC, other OBD symptoms may include abdominal bloating, discomfort and pain, feeling the need to have a bowel movement (BM) but unable to, straining, rectal pain and flatulence, among others.

In contrast to central opioid-related adverse effects which typically lessen over time, GI symptoms associated with chronic opioid use are not prone to tolerance. Thus, symptoms can persist for the duration of opioid management. This can result in important clinical consequences including increased risk for faecal incontinence, faecal impaction/bowel obstruction, bowel perforation, haemorrhoids, anal fissure, pelvic organ prolapse, pain management interruptions, as well as poor quality of life, poor workplace productivity, and increased healthcare utilization.

Current first-line therapy for OIC often centres on stool softeners and laxatives, such as bulking agents and bowel stimulants, diet and exercise, and opioid dose reduction, switching or discontinuation. However, these treatments are not directed at the primary aetiology of OIC and are often marginally or completely ineffective. Less than half of patients on opioid therapy achieve sufficient effect from related laxatives. Furthermore, these treatments may be burdensome to patients, are often associated with many side effects and may ultimately compromise pain management. In addition, two peripherally acting μ-opioid receptor antagonists have been approved in the EU and the US for use in chronic pain patients for the treatment of OIC: Movantig® (naloxegol), an oral tablet, and Relistor® (methylnaltrexone bromide), administered subcutaneously (Relistor® [methylnaltrexone], UK SmPC, January 2016; Movantig® [naloxegol], German SmPC, December 2014).

Historical experience with oral naloxone formulations for the treatment of OIC or as an additional abuse deterrent property within fixed-dose combination (FDC) products has been extensive (e.g., Valoron® N, Valoron® N retard, Suboxone®, Targin®/Targinact®/Targiniq™). NLX PR Tablets have very low systemic availability due to high first pass metabolism (<3%) and maximum free plasma concentrations are substantially below the μ-opioid receptor inhibition constant ($K_i$).

Naloxone is the semi-synthetic N-alkyl derivative of oxymorphone and a specific opioid antagonist which has no agonistic or morphine-like properties characteristic of other narcotic antagonists (e.g., nalorphine, levallorphan).

Naloxone acts by competitively binding to opioid receptors. It binds most strongly to the receptor, but shows also antagonistic activity at the κ- and δ-receptors. Since naloxone displays antagonistic activity at all opioid receptors, albeit with widely different affinities, and is devoid of any agonistic actions, it does not cause respiratory depression, even in excessive doses or in the absence of morphine intoxication.

Under normal circumstances, naloxone has no or only few pharmacological effects unless opioids with agonistic activity have been administered previously.

Naloxone is a suitable opioid antagonist for the treatment of opioid-induced constipation. Naloxone is rapidly and completely absorbed after oral administration and because the substance is subject to extensive first-pass metabolism, only small amounts of unmetabolised naloxone are available to the system. The vast majority of the applied substance is found in blood in the form of inactive or only mildly active metabolites such as naloxone-3-glucuronide or beta-6-naloxol. In suitable doses, naloxone is an ideal candidate for remedying opioid-induced constipation: in the intestine it is present as an active substance and can thus counter the paralysing effect of the opioid on the gastrointestinal tract, while after absorption it is largely metabolised during the first passage in the liver, and thereby becomes inactive. The analgesic effect of the opioids is thus not affected.

Since the paralysis does not only affect the duodenum and the upper part of the small intestine, but the entire gastrointestinal tract, the opioid-induced constipation cannot be treated successfully with a composition that releases the naloxone rapidly. WO 2011/117306 discloses a two-layer tablet, which in one layer contains an opioid agonist, and in another layer an opioid antagonist, wherein the tablet quickly releases both active substances. The advantage of this double-layer is to suppress the side effects of the opioid agonist, but it does not focus on suppression of the opioid-induced constipation.

The combined preparation Targin® is available on the market and comprises a mixture of the opioid agonist oxycodone in the form of a hydrochloric salt, and the opioid antagonist naloxone also in the form of a hydrochloric salt. In this preparation, the active substances are released in a prolonged manner. It is therefore suitable for the parallel treatment of pain and opioid-induced constipation. However, this monolithic formulation has the disadvantage that the release rates of the two active substances are fixed. Individualised treatments are therefore difficult to optimise.

In addition, infusion solutions available on the market for the treatment of opioid poisoning are only naloxone combined preparations, in which naloxone and the opiate are present in a fixed proportion to each other. However, for the treatment of opioid-induced constipation, it would be desirable to have single agent naloxone preparations, since this would allow administering naloxone both independently of the nature of the opiate and in variable doses. The desired quantity of naloxone could therefore be applied, which would lead to an optimal treatment. Naloxone single agent preparations are described in the patent literature, such as in WO 98/25613 A2. However, the release of naloxone from these compositions is dependent on the ambient pH in the gastrointestinal tract. A uniform application of naloxone to the entire gastrointestinal tract, and therefore an optimal treatment, are thus not possible with such products.

Naloxone has been used for many decades in millions of patients as solution for injection for the complete or partial reversal of opioid effects and for the diagnosis of suspected acute opioid overdosage. Furthermore, in combination with tilidine, naloxone for oral administration is marketed since more than 35 years in Germany for the treatment of severe pain without limitation of duration of use (Valoron® N, German SmPC, December 2014). In addition, an oral FDC product containing oxycodone and naloxone (Targin®, Targinact®) indicated for patients with moderate-to-severe pain is marketed within the EU since 10 years. Thus, due to its wide clinical use, the pharmacodynamic, pharmacokinetic and toxicological properties of naloxone are well known.

The non-clinical pharmacology and toxicology of naloxone (oral and parenteral) has been well characterised with much of the information available in the published literature and regulatory reviews of recently approved products containing naloxone as an oral prolonged-release formulation (e.g., Valoron® N, Tagin®/Targinact®/Targiniq™).

Yet, there is still a need to adapt and optimize dosage regimens for patients suffering from opioid induced constipation. So far fixed dosage combination of oxycodone/naloxone (e.g. Targin) have been used.

BRIEF DESCRIPTION OF THE INVENTION

The inventors surprisingly found that a specific dosage regimen comprising the administration of solid oral pharmaceutical dosage forms with defined release rates of the opioid receptor antagonist will result in specific and beneficial pharmacokinetics. These specific pharmacokinetics result in a great benefit in the treatment of patients suffering from opioid induced constipation.

Thus, in a first aspect of the invention the invention relates to a method for the treatment of patients suffering from opioid induced constipation. In particular the invention relates to a method for the treatment of a patient suffering from opioid induced constipation, the method comprising, administering an oral dosage form comprising an opioid receptor antagonist equivalent to 24 mg of naloxone hydrochloride twice daily or equivalent to 48 mg of naloxone hydrochloride once daily, characterized in that the opioid receptor antagonist has a rapid first pass metabolism with a plasma half-life of 2 hours or less in humans within the first 3 hours of oral administration of a solution, wherein the steady state pharmacokinetics of the oral dosage form result in a constant level of the opioid antagonist in the bloodstream, wherein the pharmacokinetics of the oral dosage form are independent of whether the dosage is administered once or twice daily, wherein the oral dosage form releases the opioid antagonist in a prolonged manner, wherein the amount of opioid antagonist released measured using the paddle stirrer method according to Ph. Eur. at 75 rpm in 1000 ml 0.1 N hydrochloric acid at 37° C., is 15%±5% in 1 h, is 26%±5% in 3 h, is 40%±5% in 6 h, is 55%±7% in 10 h, is 67%±8% in 15 h, and is 78%±10% in 20 h.

In a second aspect the invention relates to a solid oral dosage form suitable for use in the treatment. In particular the invention relates to a solid oral pharmaceutical dosage form comprising an opioid receptor antagonist for use in the treatment of opioid induced constipation comprising the opioid antagonist equivalent to 24 mg of naloxone hydrochloride as twice daily formulation or equivalent to 48 mg of naloxone hydrochloride as once daily formulation, characterized in that the opioid antagonist has a rapid first pass metabolism with a plasma half-life of 2 hours or less in humans within the first 3 hours of oral administration of a solution, wherein the steady state pharmacokinetics result in a constant level of the opioid antagonist in the bloodstream, wherein the pharmacokinetics are independent of whether the dosage is administered once or twice daily, wherein the oral dosage form releases the opioid antagonist in a prolonged manner, wherein the amount of opioid antagonist released measured using the paddle stirrer method according to Ph. Eur. at 75 rpm in 1000 ml 0.1 N hydrochloric acid at 37° C., is 15%±5% in 1 h, is 26%±5% in 3 h, is 40%±5% in 6 h, is 55%±7% in 10 h, is 67%±8% in 15 h, and is 78%±10% in 20 h.

DETAILED DESCRIPTION OF THE INVENTION

The invention relates to methods and compositions for the treatment of opioid induced constipation.

Opioid-induced constipation can be caused by any opioid analgesic or opioid analgesic analogue, or by any of their salts or mixtures. Examples of such analgesics are the following: alfentanil, allylprodine, alphaprodine, anileridine, benzylmorphine, bezitramide, buprenorphine, butorphanol, clonitazene, codeine, besomorphine, dextromoramide, dezocine, diampromide, diamorphone, dihydrocodeine, dihydromorphine, dimenoxadol, Dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphane, lofentanil, meperidine, meptazinol, metazocine, methadone, metopone, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphane, phenazocine, phenoperidine, piminodine, piritramide, propheptazine, promedol, properidine, propoxyphene, sufentanil, tilidine, and tramadol, wherein hydrocodone, morphine, hydromorphone, oxycodone, buprenorphine, codeine, fentanyl, levorphanol, meperidine, methadone, levomethadone, and dextromethadone are particularly preferred according to the invention.

In a first aspect the invention relates to a method of treatment of opioid induced constipation, the method comprising the administration of an oral dosage form of an opioid antagonist with defined pharmacokinetics.

In one embodiment of the invention the invention relates to a method for the treatment of a patient suffering from opioid induced constipation, the method comprising, administering an oral dosage form comprising an opioid receptor antagonist equivalent to 24 mg of naloxone hydrochloride twice daily or equivalent to 48 mg of naloxone hydrochloride once daily, characterized in that the opioid receptor antagonist has a rapid first pass metabolism with a plasma half-life of 2 hours or less in humans within the first 3 hours of oral administration of a solution, wherein the steady state pharmacokinetics of the oral dosage form result in a constant level of the opioid antagonist in the bloodstream, wherein the pharmacokinetics of the oral dosage form are independent of whether the dosage is administered once or twice daily, wherein the oral dosage form releases the opioid antagonist in a prolonged manner.

The inventors found that the treatment with an oral dosage form, which exhibits the above indicated pharmacokinetics provides a beneficial treatment for patients suffering from opioid induced constipation.

In preferred embodiments of the invention, the patient is receiving an opiate treatment with a dosage equivalent to at least 70, 80, 90, 100, 110, 120, 130, 140, 150, 160, 200, 240, 250, 300, 320, 400, or 500 mg of morphine per day. The higher the dosage of morphine equivalent, the more preferred is the embodiment.

In a more preferred embodiment of the invention the patient is receiving an opiate treatment with a dosage equivalent to 70 to 300 mg morphine, preferably equivalent to 75 to 270 mg morphine, more preferably 85 to 260 mg morphine and most preferably a dosage equivalent to 80 to 250 mg morphine per day.

Any opioid receptor antagonist is suitable for use in the invention, as long as the opioid receptor antagonist fulfils the criteria of a plasma half-life of less than two hours in humans within the first 3 hours of oral administration of a solution. In a preferred embodiment of the invention, the opioid receptor antagonist is a μ-receptor antagonist.

The daily dosage of a μ-receptor antagonist in the oral dosage form can be expressed as naloxone-equivalent dosage. This relation is likely due to the fact that naloxone also belongs to the class of μ-receptor antagonists.

In a preferred embodiment, the opioid receptor antagonist is naloxone or a derivative, in particular esthers or sulfonates, or pharmaceutically acceptable salts thereof.

The inventors found that a dosage form, having the above mentioned pharmacokinetics, allows the suitable treatment of patients with a total daily dosage of an opioid receptor antagonist equivalent to 48 mg of naloxone hydrochloride. The advantage of the dosage form and method according to the invention is that it provides greater flexibility for the treatment of the patient, by allowing an equally suitable two-dosages a day or a single dosage a day treatment.

In particular it is desirable that the oral dosage form releases the opioid receptor antagonist in a prolonged manner. The inventors found that the release rate of the opioid receptor antagonist is essential for the pharmacokinetics. In a preferred embodiment the oral dosage form used in the method of treatment releases the opioid antagonist in a prolonged manner, wherein the amount of opioid antagonist released measured using the paddle stirrer method according to Ph. Eur. at 75 rpm in 1000 ml 0.1 N hydrochloric acid at 37° C., is 15%±5% in 1 h, is 26%±5% in 3 h, is 40%±5% in 6 h, is 55%±7% in 10 h, is 67%±8% in 15 h, and is 78%±10% in 20 h.

A particular embodiment of the invention relates to a method for the treatment of a patient suffering from opioid induced constipation, the method comprising, administering an oral dosage form comprising an opioid receptor antagonist equivalent to 24 mg of naloxone hydrochloride twice daily or equivalent to 48 mg of naloxone hydrochloride once daily, characterized in that the opioid receptor antagonist has a rapid first pass metabolism with a plasma half-life of 2 hours or less in humans within the first 3 hours of oral administration of a solution, wherein the steady state pharmacokinetics of the oral dosage form result in a constant level of the opioid antagonist in the bloodstream, wherein the pharmacokinetics of the oral dosage form are independent of whether the dosage is administered once or twice daily, wherein the oral dosage form releases the opioid antagonist in a prolonged manner, wherein the amount of opioid antagonist released measured using the paddle stirrer method according to Ph. Eur. at 75 rpm in 1000 ml 0.1 N hydrochloric acid at 37° C., is 15%±5% in 1 h, is 26%±5% in 3 h, is 40%±5% in 6 h, is 55%±7% in 10 h, is 67%±8% in 15 h, and is 78%±10% in 20 h.

The invention additionally relates to an oral dosage from comprising an opioid receptor antagonist. In one embodiment the invention relates to a solid oral pharmaceutical dosage form comprising an opioid receptor antagonist for use in the treatment of opioid induced constipation comprising the opioid antagonist equivalent to 24 mg of naloxone hydrochloride as twice daily formulation or equivalent to 48 mg of naloxone hydrochloride as once daily formulation, characterized in that the opioid antagonist has a rapid first pass metabolism with a plasma half-life of 2 hours or less in humans within the first 3 hours of oral administration of a solution, wherein the steady state pharmacokinetics result in a constant level of naloxone in the bloodstream, wherein the pharmacokinetics are independent of whether the dosage is administered once or twice daily, wherein the oral dosage form releases the opioid antagonist in a prolonged manner.

The inventors found that the treatment with an oral dosage form, which exhibits the above indicated pharmacokinetics provides a beneficial treatment for patients suffering from opioid induced constipation.

In preferred embodiments of the invention, the patient is receiving an opiate treatment with a dosage equivalent to at least 70, 80, 90, 100, 110, 120, 130, 140, 150, 160, 200, 240, 250, 300, 320, 400, or 500 mg of morphine per day. The higher the dosage of morphine equivalent, the more preferred is the embodiment.

In a more preferred embodiment of the invention the patient is receiving an opiate treatment with a dosage equivalent to 70 to 300 mg morphine, preferably equivalent to 75 to 270 mg morphine, more preferably 85 to 260 mg morphine and most preferably a dosage equivalent to 80 to 250 mg morphine per day.

Any opioid receptor antagonist is suitable for use in the invention, as long as the opioid receptor antagonist fulfils the criteria of a plasma half-life of less than two hours in humans within the first 3 hours of oral administration of a solution. In a preferred embodiment of the invention, the opioid receptor antagonist is a μ-receptor antagonist.

The daily dosage of a μ-receptor antagonist in the oral dosage form can be expressed as naloxone-equivalent dosage. This relation is likely due to the fact that naloxone also belongs to the class of μ-receptor antagonists.

The inventors found that a dosage form, having the above mentioned pharmacokinetics, allows the suitable treatment of patients with a total daily dosage of an opioid receptor antagonist equivalent to 48 mg of naloxone hydrochloride. The advantage of the dosage form and method according to the invention is that it provides greater flexibility for the treatment of the patient, by allowing an equally suitable two-dosages a day or a single dosage a day treatment.

In particular, it is desirable that the oral dosage form releases the opioid receptor antagonist in a prolonged manner. The inventors found that the release rate of the opioid receptor antagonist is essential for the pharmacokinetics. In a preferred embodiment the oral dosage form used in the method of treatment releases the opioid antagonist in a prolonged manner, wherein the amount of opioid antagonist released measured using the paddle stirrer method according to Ph. Eur. at 75 rpm in 1000 ml 0.1 N hydrochloric acid at 37° C., is 15%±5% in 1 h, is 26%±5% in 3 h, is 40%±5% in 6 h, is 55%±7% in 10 h, is 67%±8% in 15 h, and is 78%±10% in 20 h.

A most preferred embodiment of the invention relates to a solid oral pharmaceutical dosage form comprising an opioid receptor antagonist for use in the treatment of opioid induced constipation comprising the opioid antagonist equivalent to 24 mg of naloxone hydrochloride as twice daily formulation or equivalent to 48 mg of naloxone hydrochloride as once daily formulation, characterized in that the opioid antagonist has a rapid first pass metabolism with a plasma half-life of 2 hours or less in humans within the first 3 hours of oral administration of a solution, wherein the steady state pharmacokinetics result in a constant level of opioid receptor antagonist in the bloodstream, wherein the pharmacokinetics are independent of whether the dosage is administered once or twice daily, wherein the oral dosage form releases the opioid antagonist in a prolonged manner, wherein the amount of opioid antagonist released measured using the paddle stirrer method according to Ph. Eur. at 75 rpm in 1000 ml 0.1 N hydrochloric acid at 37° C., is 15%±5% in 1 h, is 26%±5% in 3 h, is 40%±5% in 6 h, is 55%±7% in 10 h, is 67%±8% in 15 h, and is 78%±10% in 20 h.

The following descriptions and explanations refer to the solid dosage form to be used in the methods as well as the solid oral dosage form described above.

In a particularly preferred embodiment of the invention, the oral dosage form used in the method releases the active substance independently of the ambient pH of the gastrointestinal tract. This ensures that the entire gastrointestinal tract can be evenly and continuously supplied with the opioid receptor antagonist, or an acceptable salt thereof. A further optimisation of the treatment is thereby achieved. The pH-independent release of the active substance from the oral dosage form of the invention can be achieved through the choice of suitable pharmaceutical excipients that will be known to the person skilled in the art. Local pH values in the gastrointestinal tract are from about 1.2 (in the stomach), to about 6.8 in the colon.

The release of the active substance from the oral dosage form used in the method of the invention that is independent from the pH of the gastrointestinal tract is preferably understood to mean that the similarity factor f2 between a first in vitro release at a pH of 1.2 to 6.8 and a second in vitro release at any other pH of 1.2 to 6.8 is larger or equal to 50.

The similarity factor f2 is determined according to SHAH V. P., TSONG Y., SATHE P., & LIU J. P. (1998), "In vitro dissolution profile comparison-statistics and analysis of the similarity factor, f2", Pharmaceutical Research, 15, 889-896. Specifically, the similarity factor f2 is calculated by the following formula:

$$f_2 = 50 * \log_{10}\left(\left[1 + \frac{1}{n}\sum_{t=1}^{n}(R_t - T_t)^2\right]^{0.5} * 100\right)$$

In this equation, Rt and Tt represent the released quantities of active substance at time point t at the first and second pH. n is the number of time points. The f2 factor is determined under the following conditions: a) the minimal number of time points for one release is 3 (time point 0 is excluded); b) the time points for the first and the second pH should be equal; c) for each time point, and for each pH, the released quantity is indicated as the mean value of 12 measurements; d) no more than one mean value measured above a release of 85% can be taken into account for the calculation; e) the relative standard deviation or coefficient of variation of the release at a given pH should be smaller than 20% for the first time point and smaller than 10% for the second, and every subsequent time point.

The composition of the invention is characterised in that through the prolonged release the concentration of the opioid receptor antagonist in the plasma is low. Its maximum plasma concentration ($C_{max}$) is about 20× lower during the active course compared to a composition without prolonged release, and about 100× lower compared with an intravenously administered composition.

The inhibition of the receptors over the active course is advantageous. In addition to providing the constipation prevention effect of the opioid receptor antagonist, the low bioavailability in the system also ensures a reduced likelihood and/or severity of the side effects.

Since the naloxone inhibitory concentrations ($IC_{50}$) for opioid receptors (μ, δ and κ) are known, the assessment of the risk factor of a tablet can be calculated with the ratio $IC_{50}/C_{max}$. With the $IC_{50}$ of μ receptor, the value of $IC_{50}/C_{max}$ for a tablet according to the invention with 48 mg of naloxone is 54. In general, the higher the value of $IC_{50}/C_{max}$, the lower the risk factor of the tablet according to the invention. Hereafter all values relating to the $IC_{50}$ are for the μ receptor.

In a preferred embodiment, the composition has an $IC_{50}/C_{max}$ value of at least 30. In a more preferred embodiment, the composition has an $IC_{50}/C_{max}$ value of at least 35. In an even more preferred embodiment, the composition has an $IC_{50}/C_{max}$ value of at least 40. In the most preferred embodiment, the composition has an $IC_{50}/C_{max}$ value of at least 50.

In a further preferred embodiment of the invention, the oral dosage form comprises a matrix, which releases the active ingredient in a prolonged manner. The active substance can be released in a prolonged manner inexpensively, particularly when it is contained in a matrix that prolongs its release.

The oral dosage form according to the invention may comprise a matrix, which releases an opioid receptor antagonist such as naloxone, or a pharmaceutically acceptable salt thereof, in a prolonged manner. The matrix according to the invention is preferably a so-called scaffold matrix, which can be swelling or non-swelling, or can be a so-called eroding matrix. The matrix can also have properties of both scaffold and eroding matrixes.

In the case of a scaffold matrix, the active substance is incorporated into the matrix structure. The active substance is gradually dissolved by the digestive juices from the loaded scaffold matrix during the transport through the gastrointestinal tract. At the end of the process, the matrix scaffold is excreted in more or less unchanged form, or in a swollen form. In contrast, with an eroding matrix, the matrix is degraded, or eroded, which leads to active substance particles being exposed at the surface, and dissolved. The release rate therefore depends on the matrix degradation or erosion rate.

For the purpose of forming a largely stable scaffold matrix with an appropriate active substance release rate, a further preferred embodiment of the invention is an oral dosage form with a matrix that comprises one or several water-insoluble matrix-forming agents.

Another embodiment of the invention is an oral dosage form with a matrix that comprises one or several water-soluble matrix-forming agents.

According to a further preferred embodiment of the invention, the matrix of the oral dosage form is water-insoluble.

In an alternative embodiment of the invention, the matrix of the oral dosage form is water-soluble.

In another preferred embodiment of the invention, the matrix of the oral dosage form comprises one or several matrix-forming agents selected from the group consisting of cellulose esters, polyethylene oxide, polyvinylpyrrolidone/polyvinyl acetate mixtures, methacrylate-acrylate copolymers, waxes, fats such as glycerol esters, and fatty alcohols. The substance classes mentioned here are particularly suitable as matrix-forming agents for the oral dosage form of the invention. However, particularly preferred is the use of a mixture of polyvinyl acetate and polyvinylpyrrolidone, and/or a glycerol dibehenic acid ester as matrix-forming agent.

In a further preferred embodiment of the invention, the oral dosage form is free of film-coated, opioid receptor antagonist-containing particles, wherein the coating causes the prolonged release of the opioid receptor antagonist.

According to a further preferred embodiment of the invention, the oral dosage form can be formed by direct compression, since this is particularly inexpensive.

In a further embodiment, the oral dosage form additionally comprises at least one stabilizer, which protects the active substance. In a preferred embodiment, the at least one stabilizer is selected from the list comprising sulphur dioxide, sodium sulphite, sodium bisulphite, ascorbic acid and its derivatives and tocopherol, as well as its water- and fat-soluble derivatives, such as, for example, tocopherol acetate, sulphites, bisulphites and hydrogen sulphites of alkali, alkaline earth metals or other metals, paraben, BHA, BHT, gallates, as well as lower fatty acids, fruit acids, phosphoric acids, sorbic and benzoic acids as well as their salts, esters, derivatives and isomeric compounds, ascorbyl palmitate, lecithins, mono- and polyhydroxylated benzene derivatives, ethylenediaminetetraacetic acid and salts thereof, citraconic acid, cysteine, L-cysteine, conidendrin, diethyl carbonate, methylenedioxyphenols, cephalin, ß,ß'-dithiopropionic acid, biphenyl and other phenyl derivatives.

In a further embodiment, the oral dosage form additionally comprises at least one stabilizer, which protects the matrix. In a preferred embodiment, the at least one stabilizer is selected from the list comprising butylated hydroxytoluol, sulphur dioxide, sodium sulphite, sodium bisulphite, ascorbic acid and its derivatives and tocopherol, as well as its water- and fat-soluble derivatives, such as, for example, tocopherol acetate, sulphites, bisulphites and hydrogen sulphites of alkali, alkaline earth metals and other metals, paraben, BHA, BHT, gallates as well as lower fatty acids, fruit acids, phosphoric acids, sorbic and benzoic acids and their salts, esters, derivatives and isomeric compounds, ascorbyl palmitate, lecithins, mono- and polyhydroxylated benzene derivatives, ethylenediaminetetraacetic acid and their salts, citraconic acid, cysteine, L-cysteine, conidendrin, diethyl carbonate, methylenedioxyphenole, cephalin, ß,ß'-dithiopropionic acid, biphenyl and other phenyl derivatives.

In a further embodiment, the oral dosage form comprises at least one additive, wherein the additive is an emetic or a pungent agent drug. In a preferred embodiment, the oral dosage form comprises an additive, wherein this additive is a pungent agent, selected from the group comprising Allii sativi bulb, Asari rhizome cum herba, Calami rhizoma, capsici fructus (capsicum} capsici fructus acer (cayenne pepper), Rhizoma Curcumae Longae, Curcumae xanthorrhizae rhizoma, Galangae rhizoma, Semen Myristicae, Piperis nigri fructus (pepper), Sinapis albae (Erucae) Semen, Sinapis nigrae semen, Zedoariae rhizoma and Zingiberis rhizoma, preferably from the group consisting of capsici fructus (capsicum), capsici fructus acer (cayenne pepper) and Piperis nigri fructus (pepper).

In a preferred embodiment, the oral dosage form comprises at least one additive, wherein this additive is an emetic. In a preferred embodiment, the emetic is based on one or several substances from radix ipecacuanha (ipecac). In a preferred embodiment, the emetic is based on the substance emetine, in an alternative embodiment, the emetic is apomorphine.

In a further embodiment, the oral dosage form comprises a dye. In a preferred embodiment, the dye is selected from a group comprising red iron oxide, black iron oxide and indigo carmine.

In a further embodiment, the oral dosage form additionally comprises at least one non-steroid antirheumatic or an antihistamine.

In an alternative embodiment, the oral dosage form additionally comprises at least one water-soluble lubricant. In a preferred embodiment, the oral dosage form comprises at least one water-soluble lubricant selected from the group comprising adipic acid, fumaric acid, sodium benzoate and macrogol.

The method of treatment according to the invention and the dosage form according to the invention are particularly suitable for patients, which are laxative non-responders.

Laxatives are a common therapy for constipation. Laxatives are well known to those of ordinary skill in the art and include a variety of different agents. Categories of laxatives include, but are not limited to, cathartic laxatives, bulk forming laxatives, diphenylmethane laxatives, hyperosmotic laxatives, mineral oils, and 'saline' laxatives.

Cathartic laxatives include aloe and related preparations and extracts from species of the genus *Aloe; cascara sagrada* and related preparations and extracts of the species *Rhamnus purshiana* including casanthranol; *frangula* and related preparations and extracts of the species *Rhamnus frangula*; senna and related preparations and extracts of species of the genus *Cassia*; sennosides A and B and combinations thereof; concentrated solutions of the above; combinations of the above.

Bulk forming laxatives: methylcellulose; carboxymethylcellulose sodium; karaya and related preparations from species of the genuses *Sterculia* or *Cochlospermum*; malt soup extract; psyllium and related preparations and extracts of species of the genus *Plantago* including psyllium hydrophilic mucilloid; combinations of the above.

Diphenylmethane laxatives: bisacodyl; bisacodyl tannex; phenolphthalein; diphenylmethane derivatives; combinations of the above including, optionally, magnesium salts such as magnesium citrate or sodium phosphate buffers.

Hyperosmotic laxatives: glycerin (glycerol); sorbitol (d-glucitol).

Mineral oils: heavy liquid petrolatum; heavy mineral oil; liquid paraffin; white mineral oil.

Saline laxatives: magnesium citrate; magnesium hydroxide; magnesium sulfate; magnesium oxide; sodium phosphate; mono- and di-basic sodium phosphate; potassium bitartrate and sodium bicarbonate.

Stool softeners are well known to those of ordinary skill in the art and include a variety of different agents. Stool softeners include, but are not limited to, docusate calcium (dioctyl calcium sulfosuccinate); docusate potassium (dioctyl potassium sulfosuccinate) and docusate sodium.

Other laxatives or stool softeners include castor oil, dehydrocholic acid, lactulose, polyethylene glycols, polyethylene glycol 3350, guiafensin, poloxamer 188 (a copolymer consisting of polyethylene oxide)-poly(propylene oxide)-poly(ethylene oxide) in a weight ratio of 4:2:4), herbal teas, 1,8-dihydroxyanthraquinone, polycarbophil, soy milk, caffeine, and bentonite clay.

The dosage form and method according to the invention are also most suitable for patients with 3 or less complete spontaneous bowel movements (CSBM) per week.

CSBM are bowel movements that occur with no laxative use within 24 hours prior and leave the subject feeling completely evacuated. CSBM are evaluated daily with the help of a patient's diary or patients reports. The patient is considered to have had a CSBM, if i) the patient had a bowel movement,
ii) there was no laxative rescue medication use within 24 hours prior, and
iii) subject affirmed question 'Did you experience a feeling of complete evacuation after the bowel movement?'

In a particular embodiment the patient has two or less complete spontaneous bowel movement per week. In a more preferred embodiment the patient has one or less complete spontaneous bowel movements per week.

The dosage form and method according to the invention are additionally suitable for the treatment of patients with severe opioid induced constipation.

Severe constipation is characterized by a WGT of 65 to 180 h, preferably 65 to 150 h, more preferably of 70 to 140 h, even more preferably of 70 to 130 h, yet more preferably of 70 to 120 h, and most preferably of 70 to 110 h. Alternatively, severe constipation is characterized by a WGT of 65 hours or more, preferably 70 h or more and most preferably a WGT of 75 h or more.

The WGT time can be determined by any suitable method. However, in a preferred embodiment, the WGT time is determined using radio-opaque markers.

Alternatively, the severe constipation can be characterized by the colon transit time. CTT is defined as the WGT time minus the OCT time. OCT time can be determined by any suitable method. Preferably, OCT time is determined by the sulfasalazine/sulfapyridine method (Gramatte, T. et al.; 1991, Int. J. Clin. Pharmacol. Ther. Toxicol.; 29(4), 147-150).

According to a further embodiment of the invention, the severe constipation is characterized by a colon transit time of at least 55 h. Preferably, the severe constipation is characterized by a colon transit time of 56 to 130 h, more preferably of 60 to 120 h, even more preferably of 65 to 110 h, yet more preferably of 70 to 105 h, and most preferably of 75 to 100 h. Alternatively, severe constipation is characterized by a colon transit time of 56 hours or more, preferably 60 h or more and most preferably a colon transit time of 65 h or more.

EXAMPLES

Example 1: In Vitro Release Rates of Naloxone Oral Dosage Forms

The following tables have been analysed for their in vitro release profiles. The in vitro release profiles of the tablets were determined using a paddle stirrer apparatus (apparatus 2) with the paddle stirrer method according to Ph. Eur. (Europaisches Arzneibuch, 7th edition, 3rd supplement, 2.9.3 "Wirkstofffreisetzung aus festen Arzneiformen", pages 5519-5526) at 75 rpm in 1000 ml 0.1 N hydrochloric acid at 37° C. The amount of released naloxone was determined by UV-detection at 220 nm.

Tablet composition comprising 24 mg of naloxone hydrochloride:

| Component | Function | Amount/Unit |
|---|---|---|
| Naloxone layer | | |
| Naloxone hydrochloride | Drug substance | 24.00 mg |
| Cellulose, microcrystalline | Filler | 26.00 mg |
| Kollidon ® SR, | Retarding agent | 88.00 mg |
| Glycerol dibehenate | Retarding agent | 60.00 mg |
| Silica, colloidal anhydrous | Glidant | 4.80 mg |
| Magnesium stearate | Lubricant | 1.20 mg |
| Total Naloxone layer | | 204.00 mg |
| Total Placebo layer | | 280.00 mg |
| Core Tablet | | |
| Total bilayer tablet core | | 484.00 mg |
| Tablet coating | | |
| Opadry ® II | Dye | 14.00 mg |
| Final total tablet weight | | 498.00 mg |

Tablet composition comprising 48 mg of naloxone hydrochloride:

| Component | Function | Amount/Unit |
|---|---|---|
| Naloxone layer | | |
| Naloxone hydrochloride | Drug substance | 48.00 mg |
| Cellulose, microcrystalline | Filler | 84.00 mg |
| Kollidon ® SR, | Retarding agent | 144.00 mg |
| Glycerol dibehenate | Retarding agent | 120.00 mg |
| Silica, colloidal anhydrous | Glidant | 9.60 mg |
| Magnesium stearate | Lubricant | 2.40 mg |
| Total Naloxone layer | | 408.00 mg |
| Total Placebo layer | | 560.00 mg |
| Core Tablet | | |
| Total bilayer tablet core | | 968.00 mg |
| Tablet coating | | |
| Opadry ® II | Dye | 23.00 mg |
| Final total tablet weight | | 991.00 mg |

Figure 2:
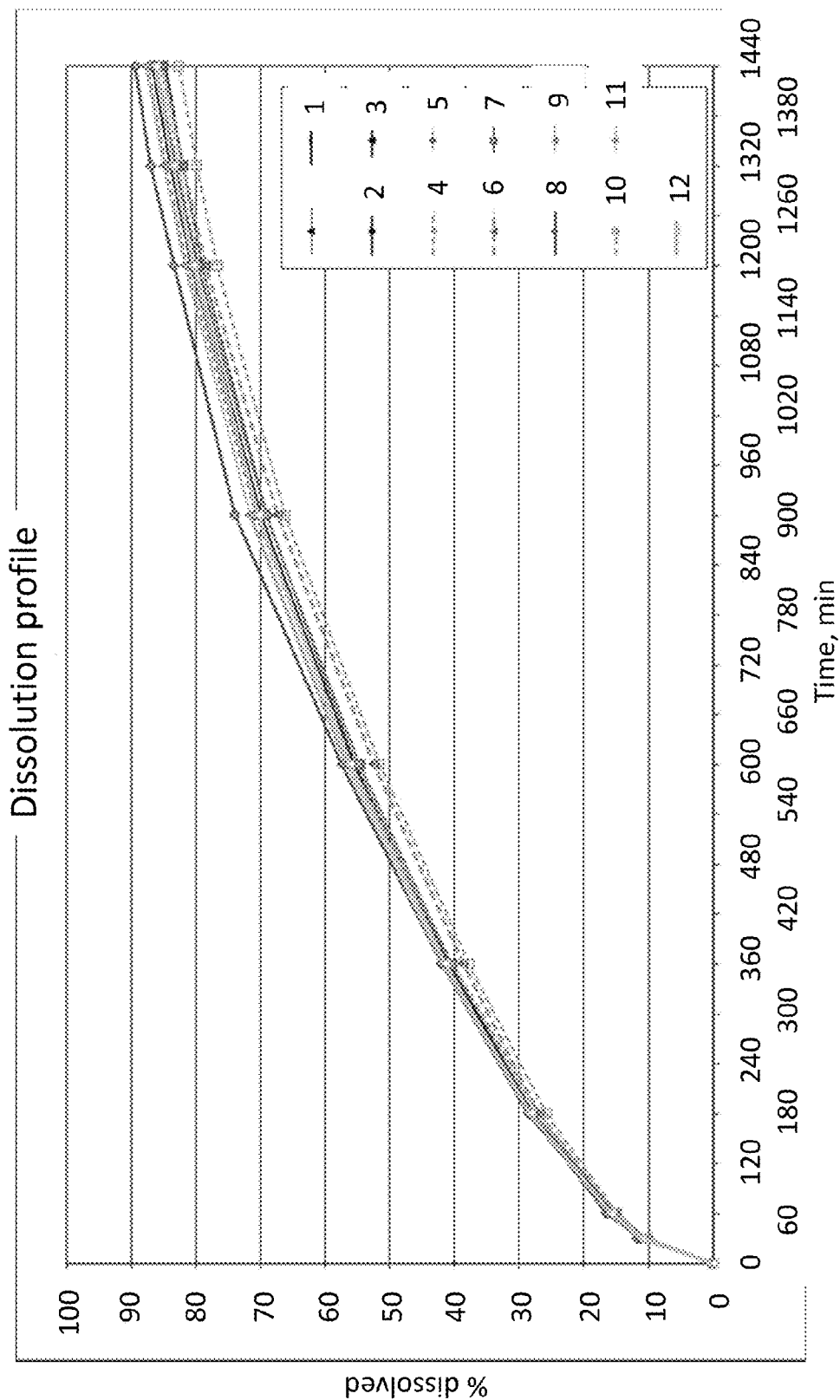

FIG. 1 shows a comparison of the mean curves of 24 mg and 48 mg tablets. FIG. 2 shows the dissolution profiles of 12 individual 24 mg tablets.

Example 2: In Vivo Study of 48 mg NLX PR Tablets

A study was designed as a randomised, open-label, crossover single-dose study of the 48 mg strength of NLX PR Tablets. In this study which was conducted in 24 healthy male and female subjects, naloxone was also administered as an immediate-release oral solution (120 ml naloxone solution containing 48 mg naloxone hydrochloride; reference product) under fasting conditions in order to characterise the prolonged-release properties of the new formulation.

Figure 3:
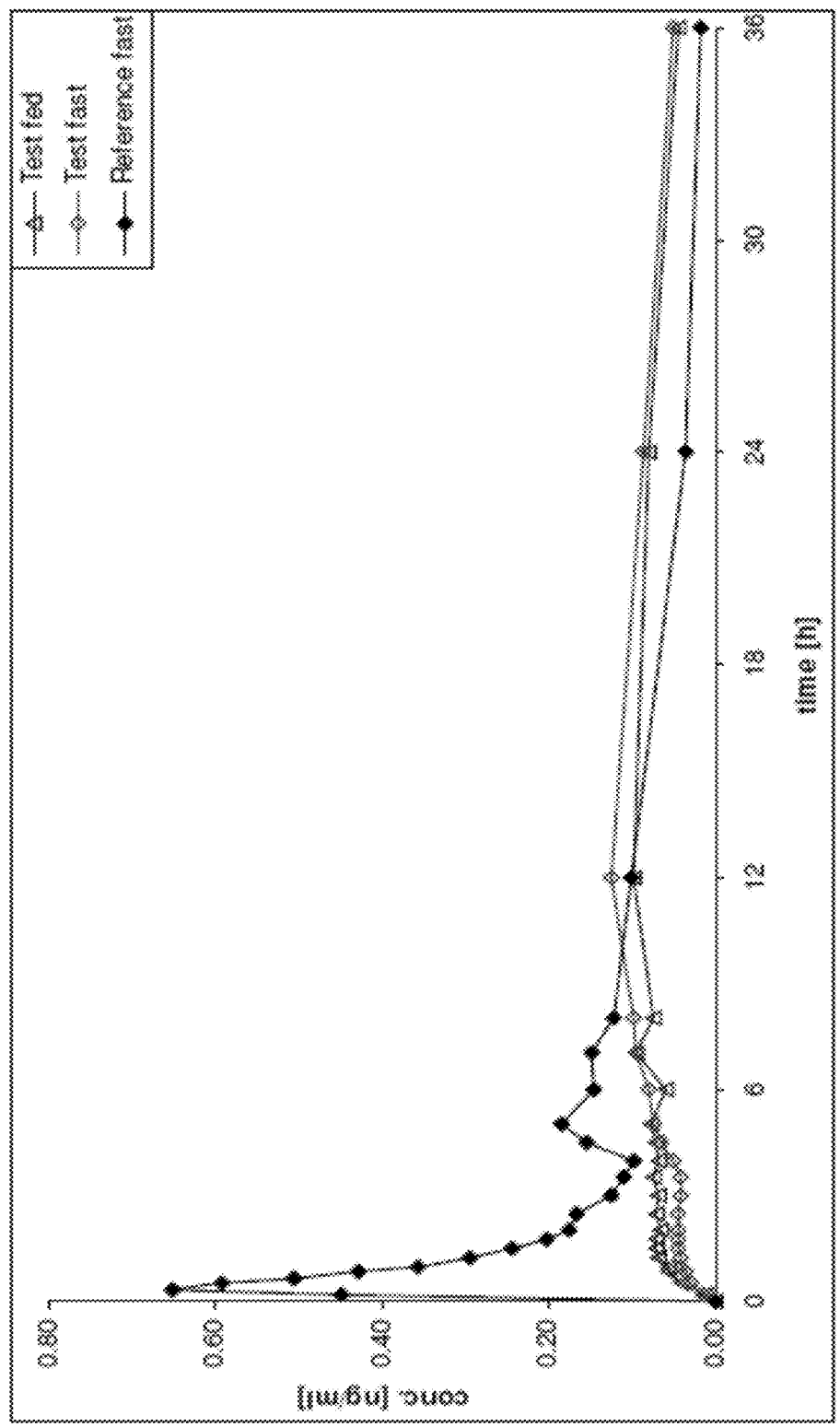

Mean plasma concentration-time profiles of naloxone after single-dose administration of 48 mg NLX PR Tablets under fasted and fed conditions and 48 mg naloxone given as oral solution in thefasted state are illustrated in the FIG. 3.

The following table summarises the mean PK parameters for naloxone.

TABLE 2

Geometric Mean (±SD) PK parameters of naloxone after single-dose administration of NLX 48 mg PR Tablets (fasted) and 48 mg naloxone as oral solution (fasted) in healthy subjects (n = 24)

|  | NLX 48 mg PRT (fasted) | 48 mg oral solution (fasted) |
| --- | --- | --- |
| Naloxone | | |
| $AUC_{(0-t)}$ [ng/mL * h] | 2.05943 | 2.70969 |
| $C_{max}$ [ng/mL] | 0.11143 | 0.70277 |
| $t_{max}$ [h] | 7.058 | 0.446 |

In the comparative bioavailability assessment of naloxone from the 48 mg NLX PR Tablets versus the oral solution (both administered under fasting conditions), the mean ratio for $AUC_{(0-t)}$ reached 76.0% (90% CI: 67.08-86.11%). Hence, systemic exposure to naloxone was significantly lower (by approximately 24%) after administration of the NLX PR Tablet as compared to the oral solution.

In general, the plasma concentration-time profiles of the parent compound following administration of the prolonged-release tablet formulation differ considerably compared to those observed for the immediate-release oral solution. In line with the prolonged-release characteristics of NLX PR Tablets, peak plasma concentrations of naloxone reached only about 25% of the peak level observed for the immediate-release oral solution. Furthermore, the NLX PR Tablet formulation showed a gradual increase in plasma concentrations with delayed occurrence of $C_{max}$ values and overall a comparably flat concentration-time curve.

FIG. 3 shows mean (arithmetic mean) plasma concentration-time curves of naloxone after single-dose administration of 48 mg NLX PR Tablets (Test, fasted and fed) and 48 mg naloxone as oral solution (Reference, fasted) in healthy subjects (n=24)

Example 3: Multiple-Dose PK of NLX 48 mg PR Tablets Once Daily Versus NLX 24 mg PR Tablets Twice Daily A study was designed to characterise the steady state pharmacokinetics of naloxone after multiple oral administration of Naloxone HCl 48 mg PR Tablets (once daily) and multiple oral administration of Naloxone HCl 24 mg PR Tablets (twice daily) under fasting conditions in 24 healthy subjects.

The study was performed as a multiple-dose, randomised, open label, two-treatment, two-period, two-sequence crossover study with 24 subjects under fasting conditions at one study site.

Two treatment periods were separated by a wash-out period of at least 7 days between consecutive administrations of study medication on clinic days.

The subjects were randomly allocated to different treatment sequences. In the first treatment period the subjects received either 4 tablets of Test product 1 or 8 tablets of Test product 2. In the second treatment period the subjects were crossovered to receive the respective other product.

Figure 4A:
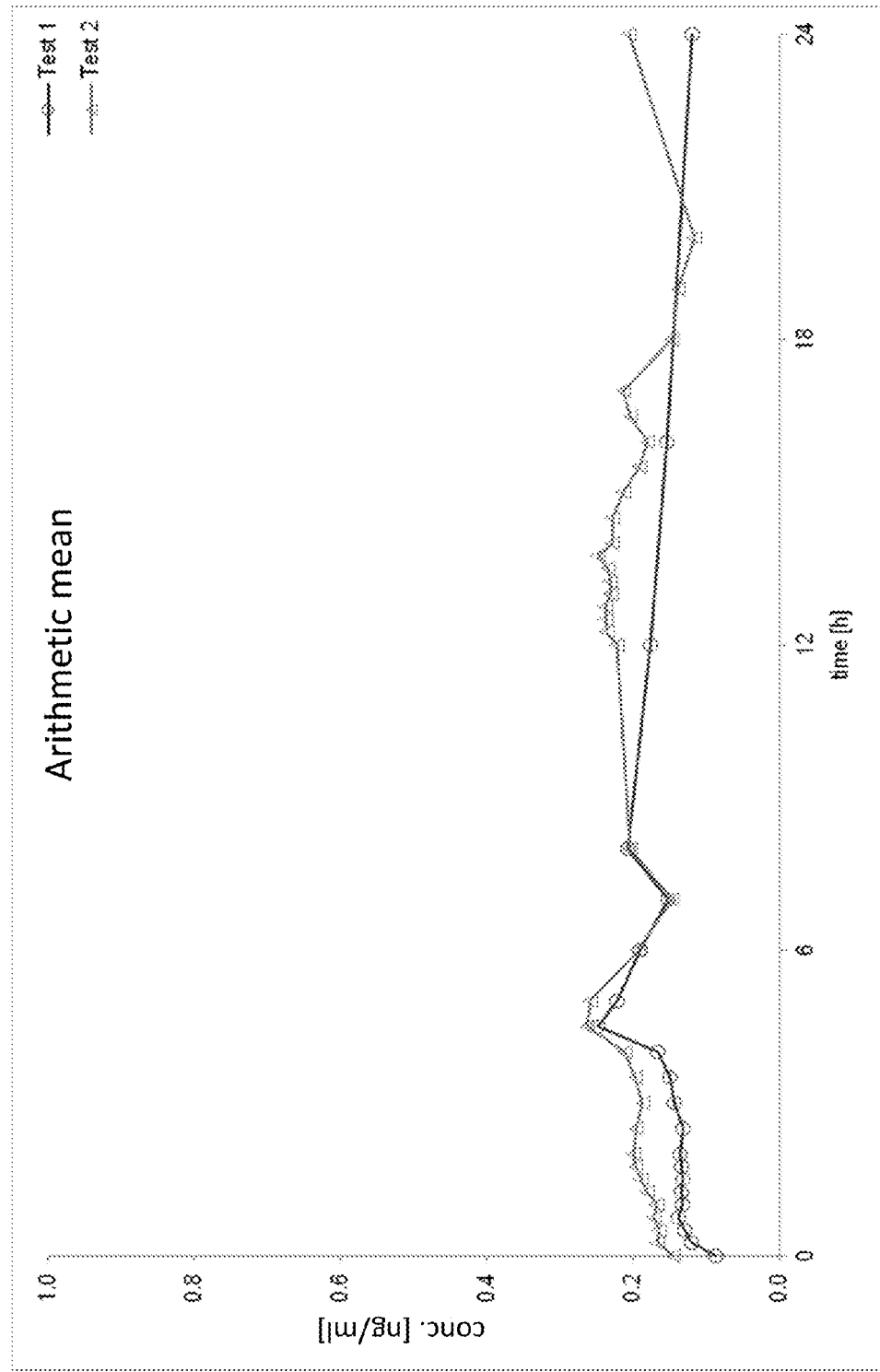
Figure 4B:
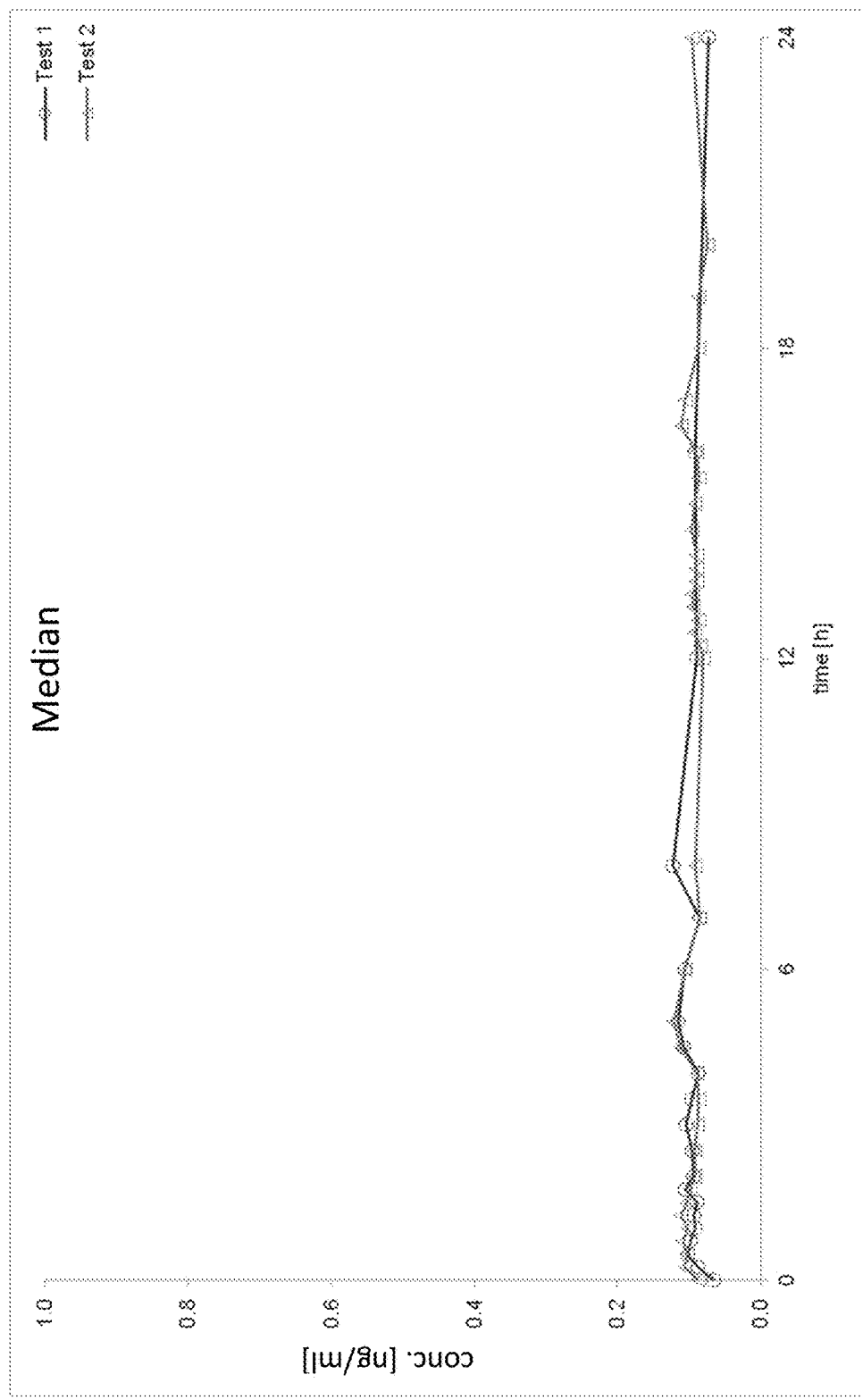

The mean plasma concentration-time curves of naloxone of the dosage interval (day 4) at steady state are shown in FIG. 4a (arithmetic mean) and FIG. 4b (median).

The mean pharmacokinetic parameters calculated for Day 4 after multiple-dose administration of 48 mg NLX PR Tablets once daily and 24 mg NLX PR Tablets twice daily are compiled in the table below.

TABLE 3

Geometric Mean of (±SD) PK parameters of naloxone after multiple-dose administration under fasting conditions of 48 mg NLX PR Tablets once daily (Day 4) and 24 mg twice daily in healthy subjects (n = 24)

|  | 48 mg once daily | 24 mg twice daily | Ratio (%) |
| --- | --- | --- | --- |
| $AUC_{(0-\tau)}$ [ng/ml * h] | 2.88769 | 3.06886 | 94.10 |
| $C_{max,ss}$ [ng/ml] | 0.20547 | 0.21949 | 93.61 |

It is evident that the plasma concentrations of naloxone are similar and constant. Thus independent of the once or twice daily dosage regimen, the pharmacokinetics are similar.

FIGURE LEGENDS

FIG. 1: Mean release profile of naloxone tablets (24 mg×/48 mg ♦) according to the invention.

FIG. 2: Comparison of the release profiles 12 tablets comprising 24 mg according to the invention.

FIG. 3: Mean (arithmetic mean) plasma concentration-time curves of naloxone after single-dose administration of 48 mg NLX PR Tablets (Test, fasted and fed) and 48 mg naloxone as oral solution (Reference, fasted) in healthy subjects (n=24)

FIGS. 4a and 4b show plasma concentration-time curves of naloxone of the dosage interval after administration of the test products. (a) Mean (arithmetic mean) plasma concentration-time curves of naloxone of the dosage interval (circles: 48 mg, 1/day; triangles: 24 mg, 2/day) (day 4) after administration of the test products (N=24); (b) Mean (median) plasma concentration-time curves of naloxone of the dosage interval (circles: 48 mg, 1/day; triangles: 24 mg, 2/day) (day 4) after administration of the test products (N=24).

The invention claimed is:

1. A method for the treatment of a patient suffering from opioid induced constipation, the method comprising, administering an oral dosage form comprising an opioid receptor antagonist equivalent to 24 mg of naloxone hydrochloride twice daily or equivalent to 48 mg of naloxone hydrochloride once daily, characterized in that the opioid receptor antagonist has a rapid first pass metabolism with a plasma half-life of 2 hours or less in humans within the first 3 hours of oral administration as a solution, wherein the steady state pharmacokinetics of the oral dosage form result in a constant level of opioid receptor antagonist in the bloodstream, wherein the pharmacokinetics of the oral dosage form are independent of whether the dosage is administered once or twice daily, wherein the oral dosage form releases the opioid antagonist in a prolonged manner, wherein the amount of opioid antagonist released measured using the paddle stirrer method according to Ph. Eur. at 75 rpm in 1000 ml 0.1 N hydrochloric acid at 37° C., is 15%±5% in 1 h, is 26%±5% in 3 h, is 40%±5% in 6 h, is 55%±7% in 10 h, is 67%±8% in 15 h, and is 78%±10% in 20 h, wherein the composition comprises a matrix, wherein the matrix comprises glycerol dibehenic acid ester as matrix-forming agent.

2. The method according to claim 1, wherein the dosage form releases the opioid antagonist independently of the ambient pH of the gastrointestinal tract.

3. The method according to claim 1, wherein the dosage form is matrix based.

4. The method according to claim 3, wherein the matrix comprises one or several matrix-forming agents selected from the group consisting of cellulose esters, polyvinylpyrrolidone/polyvinyl acetate mixtures, methacrylate-acrylate copolymers, waxes, fats such as glycerol esters, and fatty alcohols.

5. The method according to claim 1, wherein the opioid receptor antagonist in the oral dosage from is selected from the group of naloxone.

6. The method according to claim 1, wherein the oral dosage form additionally comprises an opioid receptor agonist.

7. The method according to claim 1, wherein the oral dosage form is a two-layer dosage form.

8. The method according to claim 7, characterised in that the dosage form comprises one layer comprising the opioid receptor antagonist and a second layer comprising the opioid receptor agonist.

9. Solid oral pharmaceutical dosage form comprising an opioid receptor antagonist for use in the treatment of opioid induced constipation comprising the opioid antagonist equivalent to 24 mg of naloxone hydrochloride as twice daily formulation or equivalent to 48 mg of naloxone hydrochloride as once daily formulation, characterized in that the opioid antagonist has a rapid first pass metabolism with a plasma half-life of 2 hours or less in humans within the first 3 hours of oral administration of a solution, wherein the steady state pharmacokinetics result in a constant level of opioid receptor antagonist in the bloodstream, wherein the pharmacokinetics are independent of whether the dosage is administered once or twice daily, wherein the oral dosage form releases the opioid antagonist in a prolonged manner, wherein the amount of opioid antagonist released measured using the paddle stirrer method according to Ph. Eur. at 75 rpm in 1000 ml 0.1 N hydrochloric acid at 37° C., is 15%±5% in 1 h, is 26%±5% in 3 h, is 40%±5% in 6 h, is 55%±7% in 10 h, is 67%±8% in 15 h, and is 78%±10% in 20 h, wherein the composition comprises a matrix, wherein the matrix comprises glycerol dibehenic acid ester as matrix-forming agent.

10. The solid dosage form according to claim 9, wherein the dosage form releases the opioid antagonist independently of the ambient pH of the gastrointestinal tract.

11. The solid dosage form according to claim 9, wherein the dosage form is matrix based.

12. The solid dosage form according to claim 11, wherein the matrix comprises one or several matrix-forming agents selected from the group consisting of cellulose esters, polyvinylpyrrolidone/polyvinyl acetate mixtures, methacrylate-acrylate copolymers, waxes, fats such as glycerol esters, and fatty alcohols.

13. The solid dosage form according to claim 12, characterised in that the matrix comprises polyvinylpyrrolidone/polyvinyl acetate mixtures as matrix-forming agent.

14. The solid dosage form according to claim 12, characterised in that the matrix comprises glycerine dibehenate as matrix-forming agent.

15. The solid dosage form according to claim 9, wherein the opioid receptor antagonist in the oral dosage from is selected from the group of naloxone.

16. The solid dosage form according to claim 9, wherein the oral dosage form additionally comprises an opioid receptor agonist.

17. The solid dosage form according to claim 16, wherein the opioid receptor agonist is selected from morphine, oxycodone, buprenorphine or hydromorphone.

18. The solid dosage form according to claim 9, wherein the oral dosage form is a two-layer dosage form.

19. The solid dosage form according to claim 18, characterised in that the dosage form comprises one layer comprising the opioid receptor antagonist and a second layer, which is a placebo layer.

20. The solid dosage form according to claim 18, characterised in that the dosage form comprises one layer comprising the opioid receptor antagonist and a second layer comprising the opioid receptor agonist.

* * * * *